(12) United States Patent
Danger et al.

(10) Patent No.: US 11,421,277 B2
(45) Date of Patent: Aug. 23, 2022

(54) METHODS AND COMPOSITIONS FOR PREDICTING CHRONIC LUNG ALLOGRAFT DYSFUNCTION

(71) Applicants: INSERM (INSTITUTE NATIONAL DE LA SANTE ET DE LA RECHERCHE MEDICALE), Paris (FR); UNIVERSITE DE NANTES, Nantes (FR); CENTRE NATIONAL DE LA RECHERCHE SCIENTIFIQUE, Paris (FR); CENTRE HOSPITALIER UNIVERSITAIRE DE NANTES, Nantes (FR)

(72) Inventors: Richard Danger, Reze (FR); Sophie Brouard, Suce-sur-Erdre (FR); Pierre-Joseph Royer, La Montagne (FR); Antoine Magnan, Nantes (FR)

(73) Assignees: INSERM (INSTITUTE NATIONAL DE LA SANTE ET DE LA RECHERCHE MEDICALE), Paris (FR); UNIVERSITE DE NANTES, Nantés (FR); CENTRE NATIONAL DE LA RECHERCHE SCIENTIFIQUE, Paris (FR); CENTRE HOSPITALIER UNIVERSITAIRE DE NANTES, Nantés (FR)

(*) Notice: Subject to any disclaimer, the term of this patent is extended or adjusted under 35 U.S.C. 154(b) by 49 days.

(21) Appl. No.: 16/624,061

(22) PCT Filed: Jun. 26, 2018

(86) PCT No.: PCT/EP2018/067034
§ 371 (c)(1),
(2) Date: Dec. 18, 2019

(87) PCT Pub. No.: WO2019/002247
PCT Pub. Date: Jan. 3, 2019

(65) Prior Publication Data
US 2021/0139989 A1  May 13, 2021

(30) Foreign Application Priority Data

Jun. 26, 2017 (EP) .................................. 17305788

(51) Int. Cl.
*C12Q 1/68* (2018.01)
*C12P 19/34* (2006.01)
*C12Q 1/6883* (2018.01)

(52) U.S. Cl.
CPC ...... *C12Q 1/6883* (2013.01); *C12Q 2600/112* (2013.01); *C12Q 2600/158* (2013.01)

(58) Field of Classification Search
CPC ............... C12Q 1/6883; C12Q 1/6886; C12Q 2600/158; C12Q 2600/112
See application file for complete search history.

(56) References Cited

FOREIGN PATENT DOCUMENTS

WO   2014127463 A1   8/2014

OTHER PUBLICATIONS

Sagoo, P. et al. "Development of a cross-platform biomarker signature to detect renal transplant tolerance in humans" J Clin Invest. 2010;120(6):1848-1861 (Year: 2010).*
Lande, J. D. et al. "Novel Insights into Lung Transplant Rejection by Microarray Analysis" Proc Am Thorac Soc vol. 4. pp 44-51, (Year: 2007).*
Details for HG-U133A:209995_S_AT, pp. 1-3 printed from www.affymetrix.com on Apr. 13, 2021.*
Chen, G. et al. "Discordant Protein and mRNA Expression in Lung Adenocarcinomas" Molecular & Cellular Proteomics 1.4 (2002), pp. 304-313. (Year: 2002).*
Cheung, V.G. et al. "Natural variation in human gene expression assessed in lymphoblastoid cells" Nature Genetics (Mar. 2003), vol. 33 pp. 422-425. (Year: 2003).*
Cobb, J. P. et al. "Sepsis gene expression profiling: Murine splenic compared with hepatic responses determined by using complementary DNA microarrays" Crit Care Med 2002 vol. 30, No. 12, pp. 2711-2721. (Year: 2002).*
Hoshikawa, Y. et al. "Hypoxia induces different genes in the lungs of rats compared with mice" Physiol Genomics 12: 209-219, 2003. (Year: 2003).*
Tabrizi, S.J. et al. "T Cell Leukemia/Lymphoma 1 and Galectin-1 Regulate Survival/Cell Death Pathways in Human Naive and IgM+ Memory B Cells through Altering Balances in Bcl-2 Family Proteins" The Journal of Immunology, 2009; 182:1490-1499 (Year: 2009).*
International Search Report and Written Opinion; International Application No. PCT/EP2018/067034; International Filing Date Jun. 26, 2018; dated Jul. 23, 2018; 9 pages.
Meyer, Keith C., "Lung Transplantation"; F1000prime reports; Retrieved from the Internet: URL:https://www.ncbi.nlm.nih.gov/pmc/articles/PMC3643081/pdf/medrep-05-16.pdf, Abstract; Paragraph: "Detection and Management of Chronic Lung AllograftDysfunction"; P5-16 (2013).

* cited by examiner

*Primary Examiner* — Stephen T Kapushoc
(74) *Attorney, Agent, or Firm* — Cantor Colburn LLP

(57) ABSTRACT

The present invention relates to a method for predicting the risk of having the CLAD in a subject by measuring the expression level of TCL1A in a biological sample obtained from said subject. Inventors have used a large-scale gene expression profiling of whole blood cells to identify early biomarkers of BOS. Microarray experiments performed from 80 patients (40 stable (STA) and 40 BOS) identified 47 genes differentially expressed between STA and BOS recipients. An independent set of patients (13 STA, 11 BOS) was then used for external validation by qPCR. T-cell leukemia/lymphoma protein 1A (TCL1A) gene was identified and validated as a predictive marker of BOS more than 6 months before diagnosis with area under curve of 0.77. Accordingly, the invention relates to a method for predicting the risk of having the chronic lung allograft dysfunction (CLAD) and to a method for preventing the risk of having CLAD by administering immunosuppressive drugs.

5 Claims, 2 Drawing Sheets

METHODS AND COMPOSITIONS FOR PREDICTING CHRONIC LUNG ALLOGRAFT DYSFUNCTION

CROSS REFERENCE TO RELATED APPLICATIONS

Figure 1A:
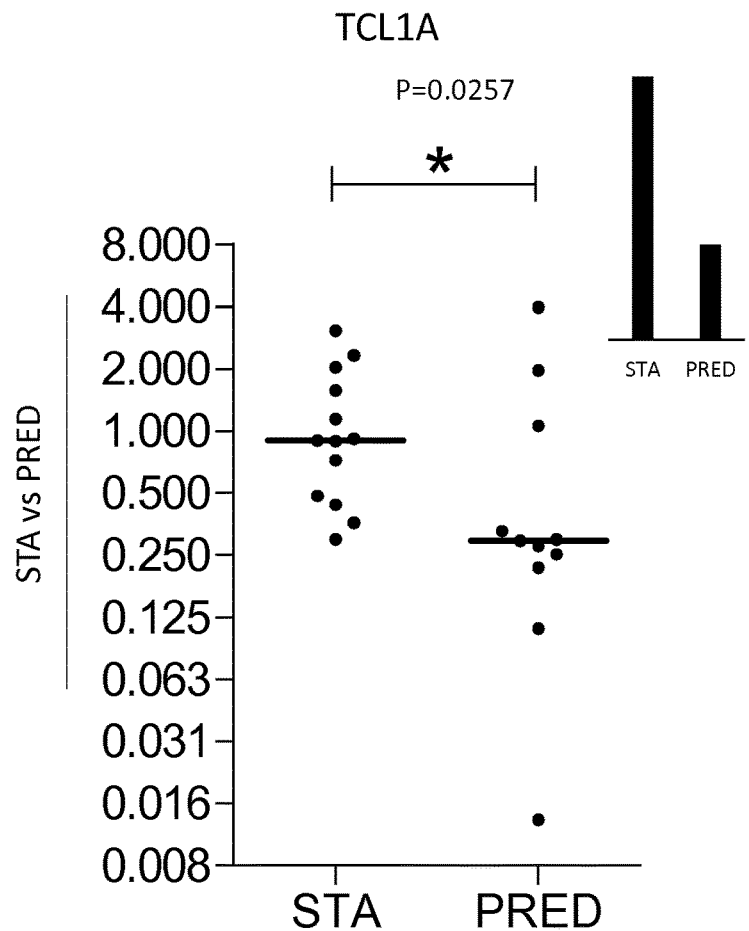

This application is a National Stage application of PCT/EP2018/067034, filed on Jun. 26, 2018, which claims the benefit of EP Application No. 17305788.6, filed on Jun. 26, 2017, both of which are incorporated by reference in their entirety herein.

FIELD OF THE INVENTION

The invention is in the field of lung transplantation, particularly, the invention allows to identify whether a subject is at risk of developing bronchiolitis obliterans syndrome.

BACKGROUND OF THE INVENTION

Chronic lung allograft dysfunction (CLAD) is the main limitation of long-term survival after lung transplantation. CLAD manifest mainly by an abnormal remodeling of the small airways resulting in progressive airflow obstruction called Bronchiolitis Obliterans Syndrome (BOS) (1-3). A restrictive ventilatory process referred as Restrictive Allograft Syndrome (RAS) has been described recently as another form of CLAD (4). The prevalence of CLAD reaches 50% at 5 years (35% BOS and 15% RAS) of lung transplant recipients. Its late diagnosis, based upon the decline of lung function, reveals an advanced degradation of the allograft. Prognosis is poor, with respectively 4 and 2 years median survival for BOS and RAS after onset. Identification of harbingers of CLAD in lung transplant recipients is thus necessary to allow proactive and targeted strategies to harness the progression of the disease, before irreversible degradation of the allograft.

It is hypothesized that CLAD arises from repeated injuries from both alloimmune and non-alloimmune mechanisms, generating fibrosis and airway obstruction (5). Tracking these inflammation and fibrotic processes has long been used to identify early signs of the disease. BAL neutrophilia, levels of regulatory T cells, chemokines/cytokines or matrix metalloproteases (MMP) have thus been suggested as early biomarkers of CLAD (6-10). More recently, expression profiling of lung biopsies pinpointed fibrosis-associated genes for the diagnosis or the prediction of CLAD (11). Yet, these invasive lung-centered approaches remained hampered by the accessibility to biological samples and are therefore limited for a routine monitoring of LTR. In blood, circulating fibrocytes or cytokine concentration have been proposed as potential biomarkers (12-15). However, these studies concerned a limited number of patients and confirmation in follow-up studies are still missing. Consequently, none of these attempts have demonstrated yet enough feasibility and robustness to achieve clinical acceptance. Accordingly, there is a need to identify new methods that allows to explore CLAD and provide early biomarkers of CLAD.

SUMMARY OF THE INVENTION

The invention relates to a method for predicting the risk of having CLAD in a subject comprising the following steps:

i) measuring the expression level of TCL1A in a biological sample obtained from said subject;
ii) comparing the expression level of TCL1A with a predetermined reference value and
iii) concluding that the subject is at risk of having CLAD when the expression level of TCL1A is lower than the predetermined reference value or concluding that the subject is not at risk of having CLAD when the expression level of TCL1A is higher than the predetermined reference value. In particular, the present invention is defined by the claims.

DETAILED DESCRIPTION OF THE INVENTION

Inventors of the present invention have used a large-scale gene expression profiling of whole blood to identify early biomarkers of CLAD. Microarray experiments performed from 80 patients (40 stable and 40 BOS) identify 47 genes differentially expressed between the stable and the BOS groups. An independent set of patients (13 stable, 11 BOS) was then used for an external validation by QPCR. TCL1A was confirmed as a predictive marker of BOS more than 6 months before the clinical diagnosis.

Method for Predicting the Risk of Having CLAD in a Subject

Accordingly, in a first aspect, the invention relates to a method for predicting the risk of having CLAD in a subject comprising the following steps: i) measuring the expression level of TCL1A in a biological sample obtained from said subject; ii) comparing the expression level of TCL1A with a predetermined reference value and iii) concluding that the subject is at risk of having CLAD when the expression level of TCL1A is lower than the predetermined reference value or concluding that the subject is not at risk of having CLAD when the expression level of TCL1A is higher than the predetermined reference value.

As used herein, the term "predicting" means that the subject to be analyzed by the method of the invention is allocated either into the group of subjects who will have CLAD, or into a group of subjects who will not have CLAD. Having CLAD referred to in accordance with the invention, particularly, means that the subject will have higher risk to develop CLAD. Typically, said risk is elevated as compared to the average risk in a cohort of transplanted subjects. In the context of the invention, the risk of having CLAD in a subject shall be predicted. The term "predicting the risk", as used herein, refers to assessing the probability according to which the patient as referred to herein will have CLAD. As will be understood by those skilled in the art, such an assessment is usually not intended to be correct for 100% of the subjects to be investigated. The term, however, requires that prediction can be made for a statistically significant portion of subjects in a proper and correct manner. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the invention allows that the prediction of an increased risk will be correct for at least 60%, at least 70%, at least 80%), or at least 90% of the subjects of a given cohort or population. The term, preferably, relates to predicting whether or not there is an increased risk of having CLAD compared to the average risk of CLAD in a population of subjects rather than giving a precise probability for the said risk.

As used herein, the term "CLAD" refers to chronic lung allograft dysfunction. CLAD is the main limitation of long term survival after lung transplantation. The prevalence of CLAD is around 50% at 5 years (35% for the BOS and 15% for the RAS phenotype). Its late diagnosis, based upon the decline of the lung functions, reveals an advanced degradation of the allograft. Prognosis is poor, with respectively 4 and 2 years median survival for BOS and RAS phenotype after disease onset.

In a particular embodiment, the method according to the invention is suitable to predict the risk of having BOS. As used herein, the term "BOS" refers to bronchiolitis obliterans syndrome. It refers to a lung disorder that is mainly associated with chronic allograft dysfunction after lung transplantation. BOS is characterized by inflammation and fibrosis of bronchiolar walls that reduce the diameter of the bronchioles and result in progressive and irreversible airflow obstruction.

In a particular embodiment, the method is suitable to predict the risk of having RAS. As used herein, the term "RAS" refers to restrictive allograft syndrome (RAS). RAS is characterized by a stair-step progression pattern, with tissue damage and fibrotic lesions occurring in the periphery of the lungs (ie, in the visceral pleura, in the alveolar interstitium and in the interlobular septa), resulting in a reduction of total lung capacity.

As used herein, the term "subject" refers to any mammals, such as a rodent, a feline, a canine, and a primate. Particularly, in the present invention, the subject is a human. In a particular embodiment, the subject is a transplanted subject. As used herein, the term "transplanted subject" also called as grafted subject, refers to a subject who has received an organ transplantation. The term "organ transplantation" refers to the procedure of replacing diseased organs, parts of organs, or tissues by healthy organs or tissues. The transplanted organ or tissue can be obtained either from the subject himself (=autograft), from another human donor (=allograft) or from an animal (=xenograft). Transplanted organs may be artificial or natural, whole (such as kidney, heart, lung and liver) or partial (such as heart valves, lung, skin and bone). In a particular embodiment, the subject is a lung transplanted subject. In particular, said lung transplanted subject may further have been grafted with the liver or the kidney, of the lung donor or of a non-related donor.

As used herein, the term "TCL1A" refers to T-cell leukemia or lymphoma protein1A which is a protein that in humans encoded by the TCL1A gene. The naturally occurring human TCL1A gene has a nucleotide sequence as shown in Genbank Accession numbers NM_021966.2 (variant 1) and NM_001098725.1 (variant 2), and the naturally occurring human TCL1A protein has an aminoacid sequence as shown in Genbank Accession numbers NP_068801.1 (variant 1) and NP_001092195.1 (variant 2). The naturally occurring murine TCL1A gene has a nucleotide sequence as shown in Genbank Accession numbers NM_009337.3 (variant 1), NM_001289468.1 (variant 2), NM_001309485.1 (variant 4) and NM_001309484.1 (variant 5) and the naturally occurring murine TCL1A protein has an amino acid sequence as shown in Genbank Accession numbers: NP_033363.1 (variant 1), NP_001276397.1 (variant 2), NP_001296414.1 (variant 4) and NP_001296413.1 (variant 5).

As used herein, the term "expression level" refers to the expression level of the TCL1A gene with further other values corresponding to the clinical parameters. Typically, the expression level of the gene may be determined by any technology known by a person skilled in the art. In particular, each gene expression level may be measured at the genomic and/or nucleic and/or protein level. In a particular embodiment, the expression level of gene is determined by measuring the amount of nucleic acid transcripts of each gene. In another embodiment, the expression level is determined by measuring the amount of each gene corresponding protein. The amount of nucleic acid transcripts can be measured by any technology known by a man skilled in the art. In particular, the measure may be carried out directly on an extracted messenger RNA (mRNA) sample, or on retrotranscribed complementary DNA (cDNA) prepared from extracted mRNA by technologies well-known in the art. From the mRNA or cDNA sample, the amount of nucleic acid transcripts may be measured using any technology known by a man skilled in the art, including nucleic microarrays, quantitative PCR, microfluidic cards, and hybridization with a labelled probe. In a particular embodiment, the expression level is determined using quantitative PCR. Quantitative, or real-time, PCR is a well-known and easily available technology for those skilled in the art and does not need a precise description. Methods for determining the quantity of mRNA are well known in the art. For example the nucleic acid contained in the biological sample is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). Preferably quantitative or semi-quantitative RT-PCR is preferred. Real-time quantitative or semi-quantitative RT-PCR is particularly advantageous. Other methods of amplification include ligase chain reaction (LCR), transcription-mediated amplification (TMA), strand displacement amplification (SDA) and nucleic acid sequence based amplification (NASBA). Nucleic acids having at least 10 nucleotides and exhibiting sequence complementarity or homology to the mRNA of interest herein find utility as hybridization probes or amplification primers. It is understood that such nucleic acids do not need to be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e. g. avidin/biotin). Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate). The nucleic acid primers or probes used in the above amplification and detection method may be assembled as a kit. Such a kit includes consensus primers and molecular probes. A kit also includes the components necessary to determine if amplification has occurred. The kit may also include, for example, PCR buffers and enzymes; positive control sequences, reaction control primers; and instructions for amplifying and detecting the specific sequences. In a particular embodiment, the method of the invention comprises the steps of providing total RNAs extracted from a biological sample and subjecting the RNAs to amplification and hybridization to specific probes, more particularly by means of a quantitative or semi-quantitative RT-PCR. In another embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a biological sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210).

As used herein, the term "biological sample" refers to any sample obtained from a transplanted subject, such as a serum sample, a plasma sample, a urine sample, a blood sample, a lymph sample, or a tissue biopsy. In a particular embodiment, biological samples for the determination of an expression level include samples such as a blood sample, a lymph sample, or a biopsy. In a particular embodiment, the biological sample is a blood sample. More particularly, the biological sample is peripheral blood mononuclear cells (PBMC). Typically, these cells can be extracted from whole blood using Ficoll, a hydrophilic polysaccharide that separates layers of blood, with the PBMC forming a cell ring under a layer of plasma. Additionally, PBMC can be extracted from whole blood using a hypotonic lysis, which will preferentially lyse red blood cells. Such procedures are known to the experts in the art.

As used herein, the term "predetermined reference value" refers to a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression level of the selected peptide in a group of reference, one can use algorithmic analysis for the statistic treatment of the expression levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher is the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

Method for Preventing the Risk of Having CLAD

In a second aspect, the invention relates to a method for preventing the risk of having CLAD in a subject comprising a step of administering to said subject a therapeutically effective amount of immunosuppressive drugs.

In the context of the invention, the term "preventing the risk" or "prophylactic treatment" as used herein, refers to treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

A "therapeutically effective amount" is intended for a minimal amount of active agent which is necessary to impart therapeutic benefit to a subject. For example, a "therapeutically effective amount" to a subject is such an amount which induces, ameliorates or otherwise causes an improvement in the pathological symptoms, disease progression or physiological conditions associated with or resistance to succumbing to a disorder.

As used herein, the term "subject" corresponds to the subject as described above. Typically, the subject is a transplanted subject. More particularly, the subject is a lung transplanted subject. In a particular embodiment, the subject is susceptible to have BOS. In another embodiment, the subject is susceptible to have RAS.

As used herein, the term "immunosuppressive drugs" also known as immunosuppressive agents or antirejection medications are drugs that inhibit or prevent the activity of immune system. Typically, the subject is treated with immunosuppressive drugs or other drugs that are currently known in the art or that will be identified in the future. In a particular embodiment, the subject is under immunosuppressive treatment, which means that the subject is administered with one or more immunosuppressive drugs. Immunosuppressive drugs that may be employed in transplantation procedures include corticosteroids, calcineurin inhibitors (cyclosporin, tacrolimus), azathioprine, mycophenolate mofetil and tyrosin kinase inhibitors (everolimus, sirolimus). These drugs may be used in monotherapy or in combination therapies. In the case of lung transplantation, the following immunosuppressive protocols are usually used. Subjects with primary lung transplantation receive an induction treatment. Protocols varies largely among centers worldwide but usually includes either injections of ATG (anti-thymocyte globulin) or basiliximab (other options are anti CD3 and anti CD5 antibodies), high dose of corticosteroids (≥1 mg/kg/day), a calcineurin inhibitor and a fourth immunosuppressive treatment (MMF or Azathioprine) or an association of high dose of corticosteroids, calcineurin inhibitors and a third immunosuppressive treatment (MMF or azathioprine). Corticotherapy is then progressively tapered to a lifelong low maintenance dose (e.g. 5 to 10 mg/day).

In a particular embodiment, the method according to the invention comprises i) determining whether the subject is at risk of having CLAD by the method as described above and ii) administering to said subject a therapeutically amount of immunosuppressive drugs when the expression level of TCL1A is lower than the predetermined reference value. Typically, the subject is administered with an increase therapeutically amount of immunosuppressive drugs.

A Method for Immunosuppressive Therapy Weaning

In a third aspect, the invention relates to a method for identifying a subject under immunosuppressive therapy as a candidate for immunosuppressive therapy weaning or minimization, comprising the steps of: i) determining whether the subject is at risk of having CLAD by the method as described above; and ii) concluding that the subject is eligible to immunosuppressive therapy weaning or minimization when the subject is not at risk of CLAD.

In a particular embodiment, the method according to the invention, wherein, the subject is at risk of having BOS.

In a particular embodiment, the method according to the invention, wherein, the subject is at risk of having RAS.

As used herein, the term "immunosuppressive therapy weaning or minimization" refers to the progressive reduction, and optionally eventually the suppression of an immunosuppressive therapy.

Kit

In another aspect, the present invention relates to a kit for determining whether a subject is at risk of having CLAD comprising at least one reagent for the determination of the expression level of TCL1A.

As used herein, the term "a reagent for the determination of an expression level" is meant a reagent which specifically allows for the determination of said expression level, i.e. a reagent specifically intended for the specific determination of the expression level of the genes comprised in the expression profile. This definition excludes generic reagents useful for the determination of the expression level of any gene, such as taq polymerase or an amplification buffer, although such reagents may also be included in a kit according to the invention.

In some embodiments, the kit according to the invention may comprise instructions for determining whether a subject is at risk of having CLAD. The instructions for determining whether a subject is at risk of having CLAD (BOS or RAS) may include at least one reference expression profile. In a particular embodiment, at least one reference expression profile is a stable expression profile. Alternatively, at least one reference expression profile may be a graft non-tolerant expression profile (e.g. expression profile obtained from a healthy subject).

The invention will be further illustrated by the following figures and examples. However, these examples and figures should not be interpreted in any way as limiting the scope of the present invention.

FIGURES

FIG. 1. qPCR validation. Microarray gene expression data (bar histograms) were validated by qPCR on an independent set of patients (dot histograms). Top panel show the comparison between STA and PRED (A) and bottom panel the STA vs DIAG comparison (B).

FIG. 2. Performance of TCL1A in prediction of BOS. (A) ROC curve for POU2AF1, TCL1A and BLK for the prediction of BOS. (B) Kaplan-Meier analysis of BOS-free survival categorized by best expression thresholds of discrimination in ROC curves.

EXAMPLE

Material & Methods
Patients
LTR were recruited within the multicentre COLT (NCT00980967) cohort. Study was approved by local ethical committee (Comitéde Protection des Personnes Ouest 1-Tours, 2009-A00036-51) and all participants provided written informed consent. Patients were defined as STA or BOS by a blind adjudication committee based upon pulmonary function tests: persistent Forced Expiratory Volume in 1 second (FEV1) decline of ≥20% from baseline for BOS group; chest imaging to confirm the diagnosis; and absence of confounding factors according to ISHLT/ERS/ATS guidelines (21, 22). Stable patients display no signs of chronic dysfunction for at least 3 years after lung transplantation. Eighty patients (40 STA and 40 BOS) were included in the identification set and 24 in the validation set (13 STA and 11 BOS).

RNA Isolation

Peripheral blood samples were collected in PAXgene tubes (PreAnalytix, Qiagen), and stored at −80° C. No infection or acute rejection were reported within one month before or after blood collection. Total RNA was extracted using the PAXgene blood RNA system kit with an on-column DNase digestion protocol according to the manufacturer's instructions. Quantity and quality of total RNA were determined using a 2100 Bioanalyzer (Agilent Technologies Incorporation). Microarray and qPCR analyses were performed on RNA with a RNA integrity number (RIN) above 6.5.

Gene Expression Microarray Analysis

Cyanin-3 and cyanin-5 labelled RNA were prepared with 100 ng of total RNA using the Two Color Agilent Low Input Quick Amp Labeling Kit following the manufacturer's instructions (Agilent Technologies Inc, Palo Alto, Calif., USA). The labeled cRNA samples were hybridized on SurePrint G3 Human Gene Expression v3 8×60K Microarrays (Agilent). Data extraction of median feature intensity was performed with Feature Extraction software v10.7 (Agilent Technologies). In order to remove signal intensity bias between each array, median feature intensities were normalized with the lowess (locally weighted scatterplot smoothing) method, then spots for which half of the samples exhibited a signal less than the mean of all median signals were removed. Correction between 2 microarray hybridization batches was performed on the 28,867 remaining spots with Combat algorithm (23) available through the R package sva (24). Normalized microarray data were deposited in the Gene Expression Ominus (GEO) database (accession number GSE94557). For identification of differential genes, Student's t-test was performed comparing STA group and each group of interest using the limma package in R. Genes with p-values inferior to 5% and fold change (FC) superior to 1.5 were considered as differentially expressed. The biological significance of selected genes was assessed using GOminer software. Only GO categories enriched with a false discovery rate (FDR) inferior to 5% and with at least 5 represented genes were selected. The cell type source of differential genes was evaluated using the gene set enrichment analysis web tool Enrichr (25).

Quantitative PCR (qPCR) for Microarray Validation

Microarray results were validated by qPCR with a set of independent samples. After reverse transcription with Superscript III (Invitrogen) real-time quantitative PCR was performed on a Taqman StepOne plus real time PCR system (Applied Biosystems) using commercially available primers: HPRT1 (Hs99999909_m1), β2M (Hs00984230_m1), ACTB (Hs99999903_m1), CD19 (Hs99999192_m1), TCL1A (Hs00951350_m1) ELANE (Hs00975994_g1), AZU1 (Hs00156049_m1), FCRL6 (Hs02341772_m1), IGLL5 (Hs04330879_u1), POU2AF1 (Hs01573371_m1), BLK (Hs01017452_m1), DEFA3 (Hs00414018_m1) and OLFM4 (Hs00197437_m1). Samples were run in duplicate and the geometric mean of quantification cycle values (Cq) for HPRT1, β2M and ACTB was used for normalization. Relative expression between a sample and a reference was calculated according to the $2-\Delta\Delta CT$ method.

Statistics

For QPCR experiments, the non-parametric Whitney test was applied using GraphPad Prism (Graphpad software, La Jolla, Calif., USA). *p<0.05, p<0.01, *p<0.001.

Results

Lung Transplant Recipients

LTR included in this study were recruited within the multicentre COLT cohort. COLT allowed a longitudinal follow up, with a patient monitoring and biocollection every 6 months after transplantation. Thanks to the longitudinal follow up, we defined two classes of BOS samples depending on the time between blood collection and CLAD diagnosis (defined as the time-point with a decline of ≥20% in FEV1 from baseline) (data not shown). Blood samples collected at least 6 months before CLAD diagnosis were incorporated in the prediction class (PRED) and blood samples collected at the time or after CLAD diagnosis (up to 13 months after diagnosis) were incorporated in the diagnosis class (DIAG) (data not shown). No patient duplicates were included within these two classes. For the stable group (STA), blood was collected 6 months and 12 months after transplantation and a comparison of these 2 time points was performed to exclude irrelevant genes altered by time post-transplantation (data not shown). LTR groups were homogeneous regarding age, sex, BMI, type of transplantation, induction treatment and infection and rejection events. Difference in azithromycin exposure was observed in the identification set between the STA and the BOS groups (52.5% vs 82.4 and 91.3%, p=0.0024). Although not significant, similar proportions were observed in the validation set (46.2% vs 87.5 and 81.8%, p=0.071). Time of blood collection was different between groups. Noteworthy, collection time for STA groups covered the collection time for the PRED groups (196 and 376 days at V3 and V4 respectively vs 260 days in the identification set; and 185 and 364 days at V3 and V4 respectively vs 311 days in the validation set).

Identification of Gene Signatures Associated with CLAD

Gene expression profiling identified a total of 47 transcripts differently expressed between STA and BOS groups (data not shown). Comparison between STA and PRED groups pinpointed 34 transcripts (52 probes) differentially expressed. GO analysis highlighted the enrichment of 6 genes related to the immune system (GO:0006955, immune response, FDR=0.031 and GO:0002376 immune system process, FDR=0.048) (data not shown), which are the genes coding for CD19 (CD19, log 2FCBOS/STA=−0.65), the major histocompatibility complex class II DQα1 (HLA-DQA1; log 2FCBOS/STA=−0.63) and DQα2 (HLA-DQA2, log 2FCBOS/STA=−0.61), the immunoglobulin lambda-like polypeptide 1 (IGLL1, log 2FCBOS/STA=−0.69), the POU class 2 associating factor 1 (POU2AF1, log 2FCBOS/STA=−0.77) and the Spi-B transcription factor (SPIB, log 2FCBOS/STA=−0.63). Analysis using Enrichr tool stressed the enrichment of genes related to CD19+ B cells including CD19, HLA-DQA1, POU2AF1, pre-B lymphocyte 3 (VPREB3, log 2FCBOS/STA=−0.76), B lymphoid tyrosine kinase (BLK, log 2FCBOS/STA=−0.66) and T-cell leukemia/lymphoma 1A (TCL1A, log 2FCBOS/STA=−0.83). Unsupervised hierarchical clustering of all expressed genes revealed that these genes resided in the same gene cluster, along with known B-cell related genes such as MS4A1 (membrane-spanning 4-domains, subfamily A, member 14 also called CD20 molecule), BANK1 (B-cell scaffold protein with ankyrin repeats 1) and CD40, reinforcing the potential association of B-cell related genes with prediction of BOS.

Comparing the STA group with the DIAG group, we highlighted 27 unique transcripts (37 probes) with significant differential expression (data not shown). GO analysis revealed genes associated with biological defense response (data not shown) (e.g. GO:0009617, response to bacterium, FDR<0.0001, GO:0006952, defense response, FDR=0.0002), namely alkaline phosphatase, liver/bone/kidney (ALPL, log 2FCBOS/STA=−0.68), azurocidin 1 (AZU1, log 2FCBOS/STA=−0.95), cathepsin G (CTSG, log 2FCBOS/STA=−0.99), defensin alpha 3 (DEFA3, log 2FCBOS/STA=−1.23), defensin alpha 4 (DEFA4, log 2FCBOS/STA=−1.23), elastase, neutrophil expressed (ELANE, log 2FCBOS/STA=−0.98), peptidoglycan recognition protein 1 (PGLYRP1, FC=−0.94) and spondin 2 (SPON2, log 2FCBOS/STA=0.62).

Noteworthy, 11 transcripts were associated with BOS both with DIAG and PRED groups including TCL1A, VPREB3 and various immunoglobulin lambda and kappa light chain variable regions.

Validation of TCL1A as a Predictive Biomarker of CLAD

Figure 1B:
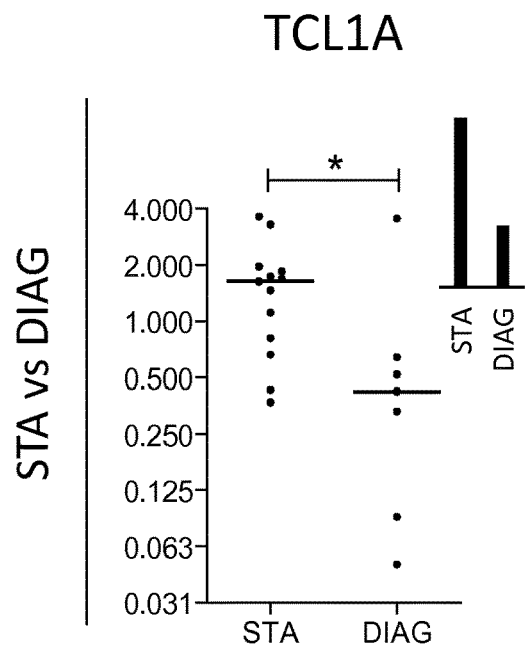
Figure 2A:
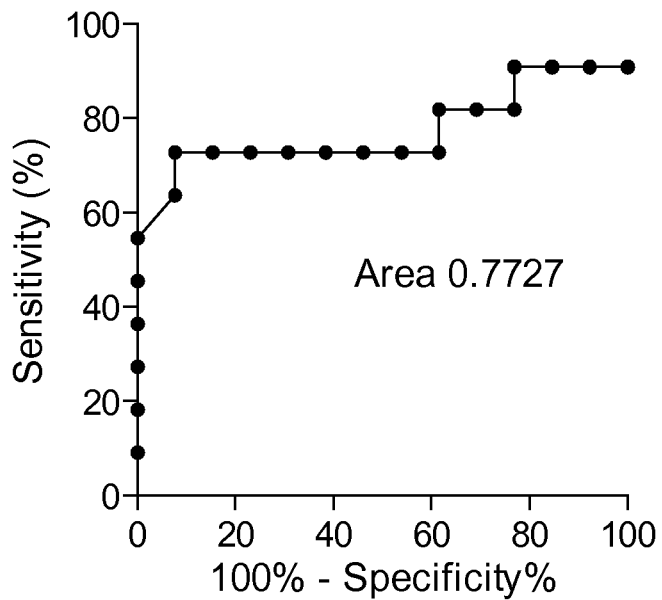
Figure 2B:
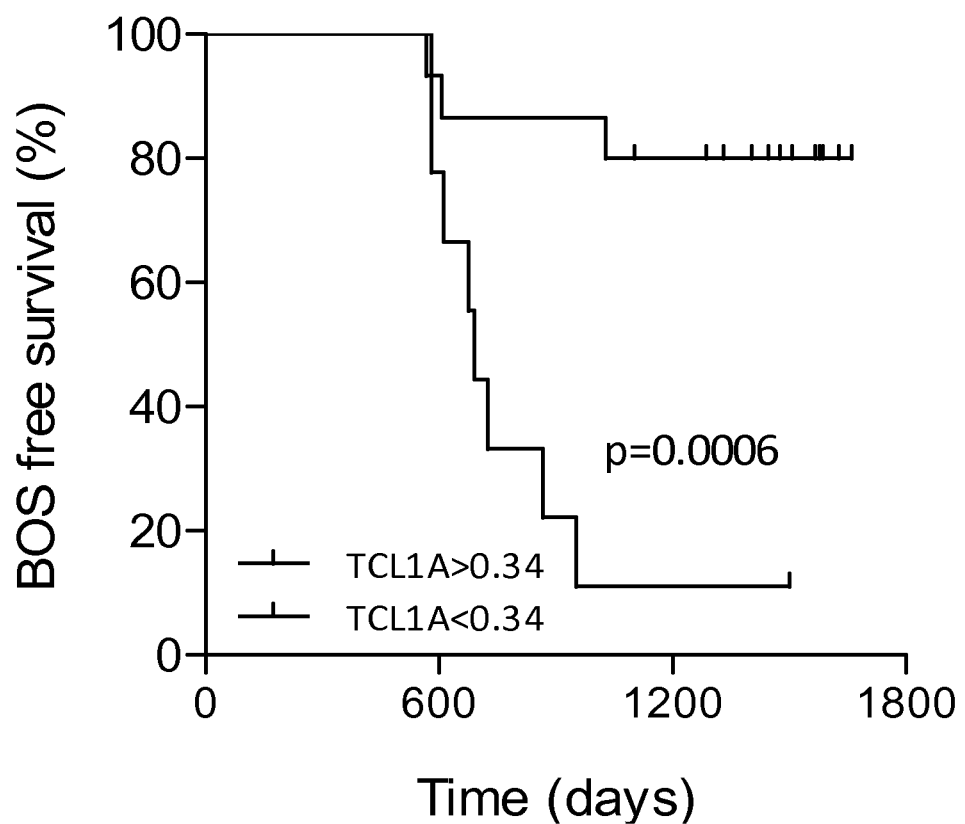

We already patented the identification of POU2AF1 and BLK as predictive biomarkers of CLAD. In addition to these biomarkers, we identified a new gene, TCL1A as another biomarker of CLAD. Ten genes selected on the basis of their p-values and fold change (FC) magnitude were measured by qPCR on an independent set of patients (data not shown). Twenty-four patients were enrolled (13 STA and 11 BOS), for respectively 11 and 8 samples in the PRED and the DIAG classes (data not shown). Downregulation of TCL1A (p=0.0257) expression in the PRED group was validated by qPCR (FIG. 1A). By contrast, the downregulation of CD19 and IGLL5 were not confirmed although a trend could be observed for CD19 (p=0.0725). Noteworthy, expression of TCL1A and BLK was constant in STA group between 6 and 12 months post transplantation (data not shown). For diagnostic purpose, we confirmed the upregulation of FCRL6 (p=0.0174) and the down regulation of TCL1A (p=0.0265) (FIG. 1B). We were unable to extrapolate the gene expression data in a set of 7 patients with a restrictive allograft syndrome (RAS) (not shown), stressing the specificity of the transcriptomic signature for the BOS subtype. TCL1A was differentially expressed in the PRED group, i.e. more than 6 months before the clinical diagnosis of BOS. We thus decided to evaluate the performance of these this marker for the prediction of the disease. ROC curve indicated that TCL1A (AUC 0.773, 95% CI=0.553 to 0.993) expression discriminated well STA from BOS patients (FIG. 2A). Global performances of the prediction show an accuracy higher of 80% for the three markers. Expression of POU2AF1, TCL1A and BLK were highly correlated (data not shown) and subsequently, performance of the prediction was not improved by the combination of the three markers (data not shown). We then performed Kaplan-Meier analyses to investigate the BOS free survival regarding TCL1A expression. As shown in FIG. 2B, level of TCL1A under 0.34 (corresponding to best expression thresholds according to ROC curves) reduced significantly the likelihood of BOS-free survival after lung transplantation (p<0.01).

As a conclusion, using whole blood profiling we identified and validated TCL1A as biomarker predictive of BOS, more than 6 months before diagnosis. This gene allow stratifying upon CLAD risk and could be easily monitored to provide clinicians with new tools to improve follow-up and adapt treatment of patient likely to develop CLAD before clinical manifestations and allograft damages.

REFERENCES

Throughout this application, various references describe the state of the art to which this invention pertains. The disclosures of these references are hereby incorporated by reference into the present disclosure.

1. Meyer K C, Raghu G, Verleden G M, Corris P A, Aurora P, Wilson K C, Brozek J, Glanville A R, ISHLT/ATS/ERS BOS Task Force Committee, ISHLT/ATS/ERS BOS Task Force Committee. An international ISHLT/ATS/ERS clinical practice guideline: diagnosis and management of bronchiolitis obliterans syndrome. Eur Respir J 2014; 44:1479-1503.

2. Royer P-J, Olivera-Botello G, Koutsokera A, Aubert J-D, Bernasconi E, Tissot A, Pison C, Nicod L, Boissel J-P, Magnan A, SysCLAD consortium. Chronic Lung Allograft Dysfunction: A Systems Review of Mechanisms. Transplantation 2016; doi:10.1097/TP.0000000000001215.

3. Sato M. Chronic lung allograft dysfunction after lung transplantation: the moving target. Gen Thorac Cardiovasc Surg 2013; 61:67-78.

4. Sato M, Keshavjee S. Bronchiolitis Obliterans Syndrome: Alloimmune-Dependent and -Independent Injury with Aberrant Tissue Remodeling. Semin Thorac Cardiovasc Surg 2008; 20:173-182.

5. Devouassoux G, Drouet C, Pin I, Brambilla C, Brambilla E, Colle P-E, Pison C, Grenoble Lung Transplant Group. Alveolar neutrophilia is a predictor for the bronchiolitis obliterans syndrome, and increases with degree of severity. Transpl Immunol 2002; 10:303-310.

6. Neurohr C, Huppmann P, Samweber B, Leuschner S, Zimmermann G, Leuchte H, Baumgartner R, Hatz R, Frey L, Ueberfuhr P, Bittmann I, Behr J, Munich Lung Transplant Group. Prognostic value of bronchoalveolar lavage neutrophilia in stable lung transplant recipients. J Heart Lung Transplant Off Publ Int Soc Heart Transplant 2009; 28:468-474.

7. Reynaud-Gaubert M, Marin V, Thirion X, Farnarier C, Thomas P, Badier M, Bongrand P, Giudicelli R, Fuentes P. Upregulation of chemokines in bronchoalveolar lavage fluid as a predictive marker of post-transplant airway obliteration. J Heart Lung Transplant 2002; 21:721-730.

8. Hübner R H, Meffert S, Mundt U, Böttcher H, Freitag S, El Mokhtari N E, Pufe T, Hirt S, Fölsch U R, Bewig B. Matrix metalloproteinase-9 in bronchiolitis obliterans syndrome after lung transplantation. Eur Respir J 2005; 25:494-501.

9. Bhorade S M, Chen H, Molinero L, Liao C, Garrity E R, Vigneswaran W T, Shilling R, Sperling A, Chong A, Alegre M-L. Decreased percentage of CD4+FoxP3+ cells in bronchoalveolar lavage from lung transplant recipients correlates with development of bronchiolitis obliterans syndrome. Transplantation 2010; 90:540-546.

10. Jonigk D, Izykowski N, Rische J, Braubach P, Kühnel M, Warnecke G, Lippmann T, Kreipe H, Haverich A, Welte T, Gottlieb J, Laenger F. Molecular Profiling in Lung Biopsies of Human Pulmonary Allografts to Predict Chronic Lung Allograft Dysfunction. Am J Pathol 2015; 185:3178-3188.

11. Shah R J, Bellamy S L, Lee J C, Cantu E, Diamond J M, Mangalmurti N, Kawut S M, Ware L B, Christie J D. Early plasma soluble receptor for advanced glycation end-product levels are associated with bronchiolitis obliterans syndrome. Am J Transplant Off J Am Soc Transplant Am Soc Transpl Surg 2013; 13:754-759.

12. Salama M, Jaksch P, Andrukhova O, Taghavi S, Klepetko W, Aharinejad S. Endothelin-1 is a useful biomarker for early detection of bronchiolitis obliterans in lung transplant recipients. J Thorac Cardiovasc Surg 2010; 140: 1422-1427.

13. Paantjens A W M, Kwakkel-van Erp J M, Van Ginkel W G J, Van Kessel D A, Van Den Bosch J M M, Van De Graaf E A, Otten H G. Serum thymus and activation regulated chemokine levels post-lung transplantation as a predictor for the bronchiolitis obliterans syndrome. Clin Exp Immunol 2008; 154:202-208.

14. LaPar D J, Burdick M D, Emaminia A, Harris D A, Strieter B A, Liu L, Robbins M, Kron I L, Strieter R M, Lau C L. Circulating fibrocytes correlate with bronchiolitis obliterans syndrome development after lung transplantation: a novel clinical biomarker. Ann Thorac Surg 2011; 92:470-477.

15. Anglicheau D, Suthanthiran M. NONINVASIVE PREDICTION OF ORGAN GRAFT REJECTION AND OUTCOME USING GENE EXPRESSION PATTERNS. Transplantation 2008; 86:192-199.

16. Brouard S, Mansfield E, Braud C, Li L, Giral M, Hsieh S, Baeten D, Zhang M, Ashton-Chess J, Braudeau C, Hsieh F, Dupont A, Pallier A, Moreau A, Louis S, Ruiz C, Salvatierra O, Soulillou J-P, Sarwal M. Identification of a peripheral blood transcriptional biomarker panel associated with operational renal allograft tolerance. Proc Natl Acad Sci USA 2007; 104:15448-15453.

17. Naesens M, Khatri P, Li L, Sigdel T K, Vitalone M J, Chen R, Butte A J, Salvatierra O, Sarwal M M. Progressive histological damage in renal allografts is associated with expression of innate and adaptive immunity genes. Kidney Int 2011; 80:1364-1376.

18. Chen Y, Zhang H, Xiao X, Jia Y, Wu W, Liu L, Jiang J, Zhu B, Meng X, Chen W. Peripheral blood transcriptome sequencing reveals rejection-relevant genes in long-term heart transplantation. Int J Cardiol 2013; 168:2726-2733.

19. Martínez-Llordella M, Lozano J J, Puig-Pey I, Orlando G, Tisone G, Lerut J, Benítez C, Pons J A, Parrilla P, Ramírez P, Bruguera M, Rimola A, Sánchez-Fuego A. Using transcriptional profiling to develop a diagnostic test of operational tolerance in liver transplant recipients. J Clin Invest 2008; 118:2845-2857.

20. Kurian S M, Fouraschen S M G, Langfelder P, Horvath S, Shaked A, Salomon D R, Olthoff K M. Genomic profiles and predictors of early allograft dysfunction after human liver transplantation. Am J Transplant Off J Am Soc Transplant Am Soc Transpl Surg 2015; 15:1605-1614.

21. Meyer K C, Raghu G, Verleden G M, Corris P A, Aurora P, Wilson K C, Brozek J, Glanville A R, ISHLT/ATS/ERS BOS Task Force Committee, ISHLT/ATS/ERS BOS Task Force Committee. An international ISHLT/ATS/ERS clinical practice guideline: diagnosis and management of bronchiolitis obliterans syndrome. Eur Respir J 2014; 44:1479-1503.

22. Verleden G M, Raghu G, Meyer K C, Glanville A R, Corris P. A new classification system for chronic lung allograft dysfunction. J Heart Lung Transplant 2014; 33:127-133.

23. Johnson W E, Li C, Rabinovic A. Adjusting batch effects in microarray expression data using empirical Bayes methods. Biostat Oxf Engl 2007; 8:118-127.

24. Leek J T, Johnson W E, Parker H S, Jaffe A E, Storey J D. The sva package for removing batch effects and other unwanted variation in high-throughput experiments. Bioinformatics 2012; 28:882-883.

25. Kuleshov M V, Jones M R, Rouillard A D, Fernandez N F, Duan Q, Wang Z, Koplev S, Jenkins S L, Jagodnik K M, Lachmann A, McDermott M G, Monteiro C D, Gundersen G W, Ma'ayan A. Enrichr: a comprehensive gene set enrichment analysis web server 2016 update. Nucleic Acids Res 2016; 44:W90-97.

26. Budding K, van de Graaf E A, Kardol-Hoelhagel T, Kwakkel-van Erp J M, Luijk B D, Oudijk E-J D, van Kessel D A, Grutters J C, Hack C E, Otten H G. Soluble CD59 is a Novel Biomarker for the Prediction of Obstructive Chronic Lung Allograft Dysfunction After Lung Transplantation. Sci Rep 2016; 6:26274.

27. Jaksch P, Taghavi S, Klepetko W, Salama M. Pretransplant serum human chitinase-like glycoprotein YKL-40 concentrations independently predict bronchiolitis obliterans development in lung transplant recipients. J Thorac Cardiovasc Surg 2014; 148:273-281.

28. Suwara M I, Vanaudenaerde B M, Verleden S E, Vos R, Green N J, Ward C, Borthwick L A, Vandermeulen E, Lordan J, Van Raemdonck D E, Corris P A, Verleden G M, Fisher A J. Mechanistic differences between phenotypes of chronic lung allograft dysfunction after lung transplantation. Transpl Int Off J Eur Soc Organ Transplant 2014; 27:857-867.

29. Luo Y, Fujii H, Gerster T, Roeder R G. A novel B cell-derived coactivator potentiates the activation of immunoglobulin promoters by octamer-binding transcription factors. Cell 1992; 71:231-241.

30. Brunner C, Sindrilaru A, Girkontaite I, Fischer K-D, Sunderkötter C, Wirth T. BOB.1/OBF.1 controls the balance of TH1 and TH2 immune responses. EMBO J 2007; 26:3191-3202.

31. Stauss D, Brunner C, Berberich-Siebelt F, Höpken U E, Lipp M, Müller G. The transcriptional coactivator Bob1 promotes the development of follicular T helper cells via Bcl6. EMBO J 2016; 35:881-898.

32. Dymecki S M, Niederhuber J E, Desiderio S V. Specific expression of a tyrosine kinase gene, blk, in B lymphoid cells. Science 1990; 247:332-336.

33. Simpfendorfer K R, Armstead B E, Shih A, Li W, Curran M, Manjarrez-Orduño N, Lee A T, Diamond B, Gregersen P K. Autoimmune disease-associated haplotypes of BLK exhibit lowered thresholds for B cell activation and expansion of Ig class-switched B cells. Arthritis Rheumatol Hoboken N.J. 2015; 67:2866-2876.

34. Laine J, Künstle G, Obata T, Sha M, Noguchi M. The protooncogene TCL1 is an Akt kinase coactivator. Mol Cell 2000; 6:395-407.

35. Baron D, Ramstein G, Chesneau M, Echasseriau Y, Pallier A, Paul C, Degauque N, Hernandez-Fuentes M P, Sanchez-Fueyo A, Newell K A, Giral M, Soulillou J-P, Houlgatte R, Brouard S. A common gene signature across multiple studies relate biomarkers and functional regulation in tolerance to renal allograft. Kidney Int 2015; 87:984-995.

36. Roux A, Bendib Le Lan I, Holifanjaniaina S, Thomas K A, Hamid A M, Picard C, Grenet D, De Miranda S, Douvry B, Beaumont-Azuar L, Sage E, Devaquet J, Cuquemelle E, Le Guen M, Spreafico R, Suberbielle-Boissel C, Stern M, Parquin F, Foch Lung Transplantation Group. Antibody-Mediated Rejection in Lung Transplantation: Clinical Outcomes and Donor-Specific Antibody Characteristics. Am J Transplant Off J Am Soc Transplant Am Soc Transpl Surg 2016; doi:10.1111/ajt.13589.

37. Le Pavec J, Suberbielle C, Lamrani L, Feuillet S, Savale L, Dorfmüller P, Stephan F, Mussot S, Mercier O, Fadel E. De-novo donor-specific anti-HLA antibodies 30 days after lung transplantation are associated with a worse outcome. J Heart Lung Transplant Off Publ Int Soc Heart Transplant 2016; 35:1067-1077.

38. Tikkanen J M, Singer L G, Kim S J, Li Y, Binnie M, Chaparro C, Chow C-W, Martinu T, Azad S, Keshavjee S, Tinckam K. De Novo D Q Donor-Specific Antibodies Are Associated with Chronic Lung Allograft Dysfunction after Lung Transplantation. Am J Respir Crit Care Med 2016; 194:596-606.

39. Girnita A L, McCurry K R, Yousem S A, Pilewski J, Zeevi A. Antibody-mediated rejection in lung transplantation: case reports. Clin Transpl 2006; 508-510.

The invention claimed is:

1. A prognostic method for determining that a subject is at risk of having bronchiolitis obliterans syndrome (BOS) and preventing BOS, comprising:
   i) measuring an expression level of TCL1A in a biological sample obtained from said subject;
   ii) detecting that the expression level of TCL1A in the biological sample is lower than a predetermined reference value,
   iii) concluding that the subject is at risk of having BOS, and
   iv) administering to the subject at risk of having BOS a therapeutic amount of immunosuppressive drug to prevent BOS,
   wherein the subject is a human lung transplant recipient, and the predetermined reference value is expression level of TCL1A detected in a same biological sample type obtained from a human lung transplant recipient with a stable transplant, and
   wherein the biological sample comprises a blood sample, a lymph sample, or a combination thereof.

2. A method for immunosuppressive therapy weaning or minimization for a subject under immunosuppressive therapy, comprising:
   i) measuring an expression level of TCL1A in a biological sample obtained from the subject;
   ii) detecting that the expression level of TCL1A is greater than a predetermined reference value;
   iii) concluding that the subject is not at risk of having bronchiolitis obliterans syndrome (BOS);
   iv) concluding that the subject is eligible for immunosuppressive therapy weaning or minimization; and
   iv) administering to the subject not at risk of having BOS a progressive reduction of a therapeutic amount of immunosuppressive drugs to prevent BOS,
   wherein the subject is a human lung transplant recipient and the predetermined reference value is expression level of TCL1A detected in a same biological sample type obtained from a human lung transplant recipient with a stable transplant, and
   wherein the biological sample comprises a blood sample, a lymph sample, or a combination thereof.

3. The method of claim 1, wherein the expression level of TCL1A lower than the predetermined reference value is determined using a Receiver Operating Characteristic (ROC) curve with an area under the curve (AUC) greater than 0.7.

4. The method of claim 1, wherein the expression level of TCL1A higher than the predetermined reference value is determined using a Receiver Operating Characteristic (ROC) curve with an area under the curve (AUC) greater than 0.7.

5. The method of claim 1, wherein measuring expression level of TCL1A in a biological sample comprises measuring mRNA expression of TCL1A in the biological sample.

* * * * *